United States Patent [19]
Surdut et al.

[11] Patent Number: 5,553,503
[45] Date of Patent: Sep. 10, 1996

[54] MEASUREMENT OF FLUID PRESSURE SUCH AS BLOOD PRESSURE

[75] Inventors: Raymond J. Surdut, East Providence; Edwin H. Benz, Sr., Providence, both of R.I.; James P. Skoutas, Palm Beach Gardens, Fla.

[73] Assignee: ManometRx Group Ltd, East Providence, R.I.

[21] Appl. No.: 320,331

[22] Filed: Oct. 11, 1994

[51] Int. Cl.$^6$ ........................................... G01B 7/16
[52] U.S. Cl. .................................... 73/778; 73/760
[58] Field of Search ............... 73/760, 727, 862.04, 73/862.68, 778; 128/627

[56] References Cited

U.S. PATENT DOCUMENTS

| | | | |
|---|---|---|---|
| 4,023,562 | 5/1977 | Hynecek et al. | 73/420 |
| 4,269,193 | 5/1981 | Eckerle | 128/672 |
| 4,413,202 | 11/1983 | Krempl et al. | 73/778 |
| 4,578,613 | 5/1986 | de Boer | 310/800 |
| 4,737,676 | 4/1988 | Engel | 310/330 |
| 4,782,469 | 11/1988 | Granz | 367/157 |
| 4,833,659 | 5/1989 | Geil | 367/155 |
| 4,975,616 | 12/1990 | Park | 310/339 |
| 5,033,471 | 7/1991 | Yokoe | 128/681 |
| 5,131,401 | 7/1992 | Westenskow et al. | 128/741 |
| 5,159,228 | 10/1992 | Schaetzle | 310/338 |
| 5,288,551 | 2/1994 | Sato et al. | 428/334 |
| 5,429,006 | 7/1995 | Tamori | 73/862.046 |

Primary Examiner—Richard Chilcot
Assistant Examiner—Max Noori
Attorney, Agent, or Firm—Ellen C. Childress, P.A.

[57] ABSTRACT

Circuitry and a sensor suitable for measuring blood pressure is described. The sensor of the present invention has a flexible piezoelectric material covering the opening of a chamber. The chamber contains an electrically nonconductive, elastomeric material, and needs no pump to pressurize the chamber. An array of sensors and circuitry for measurement of fluid pressure fluctuation in a flexible environment is given.

21 Claims, 14 Drawing Sheets

MEASUREMENT OF FLUID PRESSURE SUCH AS BLOOD PRESSURE

FIELD OF THE INVENTION

This invention relates to the measurement of pressure of a fluid pumped through a flexible tube contained in a flexible environment such as blood pressure.

BACKGROUND OF THE INVENTION

Blood circulates from the heart through arteries, capillaries and veins and back to the heart to be recirculated. When leaving the heart it measures as a higher (systolic) pressure when the heart contracts, for example in a normal range of about 120 mm Hg, and a lower (diastolic) of about for example in a normal range of 80 mm Hg as the heart relaxes. Measurement of pressure is important as high blood pressure can indicate such problems as kidney disease or toxemia and low blood pressure can indicate shock.

Measurement is usually made with a sphygmomanometer, a device having an inflatable cuff connected to a measuring device, often a clear tube containing mercury. The cuff is placed around a limb and inflated until it compresses an artery until blood flow stops. This temporarily shuts off the blood flow of the artery, and mercury rises in the tube. As the cuff is slowly deflated, mercury drops in the tube. With a stethoscope, the operator listens for the flow of blood to begin, indicating pressure in the cuff is just below the pressure in the artery. At this point, a note of mercury height is made. The cuff is further slowly deflated until the beating sound disappears and blood flows more steadily. This gives a systolic reading. Such a device is uncomfortable and limits readings to highest and lowest, rather than continuous pressures, and is time consuming. Further, locations at which a cuff device can be used are limited to areas where the cuff can be wrapped around a limb. Further the cuff is sensitive to physiology of the subject, requiring different sizes for average, small and large limbs and varies with position of the limb relative to the subject's body.

The diastolic and systolic blood pressures represent approximate points of a continually varying pressure curve.

The two methods of obtaining accurate continuous total blood pressure are surgical insertion of a sensor into the artery or employment of doppler (sound) to measure a series of echoes as blood passes a particular point.

Surgical process is invasive and carries with it all of surgery's undesirable risks including anaesthesia and infection. Doppler devices are considered to be of equal accuracy to pressure sensors inserted surgically, but are limited in requiring large support equipment to receive, analyze, record and report the data obtained. Surgically inserted sensors also have a shelf-life of only a few months and are intended to be non-reusable. Doppler devices require application of conductive ointments to achieve maximum function.

In heart tissue, electrical Charges are continually generated within specific clusters of cells, accumulating an electrical potential in each cluster similar to electrical build-up in a Van de Graaf generator. When the stored electrical charge exceeds the storage capacity of each cluster, the clusters (ideally) discharge simultaneously, causing the heart muscle to contract. As the heart contracts, accumulated fluid (i.e. blood in the heart chamber) is forced through a flexible tube (i.e. artery) and through the pipeline of arteries and capillaries and eventually returns to the chamber through the venous system.

This is mechanically analogous to a piston type pumping system which circulates water in a municipal water supply, as distinguished from a rotating circulating pump.

An electrocardiograph measures the buildup and discharge of electrical charges in the heart, but does not measure the blood pressure.

With each contraction, the heart muscle generates pressure on the blood which is forced into the closed environment of the arterial system which is contained in other tissue resulting in pressure of fluid against the walls of the arterial tubes, creating a contained force at each position along the arterial tubes.

Piezoelectricity is a reversible relationship between mechanical and electrostatic stress exhibited by certain crystals which lack a center of symmetry. For example, when pressure is applied to a piezoelectric crystal such as quartz, positive and negative electric charges appear on opposite crystal faces. Replacing pressure with tension reverses the sign of the electrical charges. Piezoelectric systems are used as sensors because they are sensitive to slight changes in pressure and have an electrical output which is easily amplified for display.

Blood pressure is essentially a varying pressure in a flexible tube encased in a flexible environment where a fluid is moved by varying pressures through the tube. Since piezoelectric crystals respond to mechanical stress, it has been attempted to measure blood pressure noninvasively with piezoelectric crystals. U.S. Pat. No. 4,269,193 discloses such a device. However, gas or air is used to press on the artery, and the transducer must be capable of sensing force applied to the artery. The array uses individual silicon rectangular chips which are relatively difficult and expensive to make and use. Further, the device has proved less than satisfactory.

U.S. Pat. No. 5,033,471 discloses a means for measuring blood pressure, without use of a separate cuff, and suggests possible use of a piezoelectric sensor for detecting a pulse wave. However, a pump for applying pressure is still required.

Other materials than crystals are known which demonstrate piezoelectric properties, or can be manipulated to demonstrate such properties. Such materials are used in sonic sensors. U.S. Pat. No. 4,578,613 discloses an electroacoustic device with two sheets of foil stretched about a curve in perpendicular directions. The foil has been permanently altered to provide directional piezoelectric action on a curved surface. The second foil measures perpendicular strain. A suggested use is amplification of acoustic signals. The piezoelectric material is overstretched precharged polymeric film.

U.S. Pat. No. 4,737,676 discloses a piezoelectric transducer for measuring mechanical quantities in hollow bodies which can be used at temperatures exceeding 80 degrees C. This is given as a temperature which limits piezo-effects in many piezo-polymer materials. Material supporting the metallic portion of the film is flexible and forms a transducer.

U.S. Pat. No. 4,833,659, incorporated herein by reference, shows a sonar system with solid material between piezoelectric films, for damping the signal.

U.S. Pat. Nos. 4,782,469 and 5,159,228 disclose piezoelectric sensors for use in ultrasonic detection designed to withstand shock waves.

There is a need for a suitable piezoelectric sensor and apparatus which is compact, reusable, can externally measure dynamic pressure in a flexible conduit in a flexible environment such as an artery, is usable in a variety of sites, and in human and veterinary practice will directly and continuously monitor arterial pressure and is economical to manufacture.

There also exists a need for a compact apparatus having at least the same measurement capabilities as the inserted sensor and the doppler devices, which will measure pressure force at each point along an arterial tube system and process the measurements into quantifiable data.

The state of the art establishing the need for and lack of blood pressure measurement devices with such capabilities is demonstrated in "DEFENSE TECHNOLOGY CONVERSION, REINVESTMENT, AND TRANSITION ASSISTANCE", Small business innovation Research (SBIR) Program solicitation dated May 1993, at page 19 from the Advanced Research Projects Agency (ARPA) of the Department of Defense and other agencies:"Objective: Advance sensor technology and information technology to speed care to trauma cases. Special emphasis on (1) non-invasive sensing, (2) portable laboratory testing, and (3) medical imaging devices.

Description: There is a need for timely medical information to support decisions at the injury scene/battlefield to plan and manage overall responses. Survival rates decrease dramatically if treatment is delayed for more than one hour . . . . There is a need for non-invasive sensing of vital signs and body chemistry which can acquire information continuously, even prior to injury or illness, and transmit this information . . . ; and advanced, mobile, low powered medical imaging devices that provide for field/remote use."

SUMMARY OF THE INVENTION

The sensor of the present invention has a flexible electrically nonconductive film sandwiched between two flexible metallic layers (one for the positive side and one for the negative side). One metallic layer is connected to a positive and the other metallic layer to a negative electrical output. Neutral electrically nonconductive housing surrounds the perimeter of the sandwich and forms a closed chamber above the film. The chamber contains an electrically nonconductive, compressible, elastomeric material such as air. A protective neutral layer on the sensor rests directly on the surface of the flexible environment. There is no need for a pump to pressurize the chamber.

Circuitry, suitable for miniaturization, for measurement of continuous pressure and pressure fluctuation in a flexible environment is given.

DETAILED DESCRIPTION OF THE PREFERRED EMBODIMENTS

Figure 1:
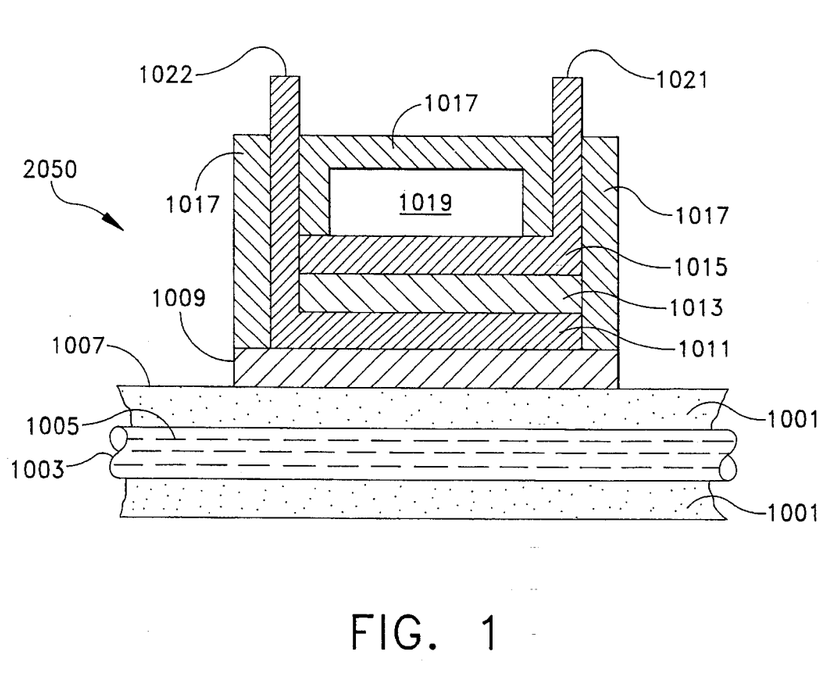
FIG. 1 is a cross sectional view of one embodiment of a sensor according to the present invention.

The sensor (2050) of FIG. 1 has a flexible electrically nonconductive film (1013), or other flexible electrically nonconductive material such as KYNAR PIEZO FILM available from AMP, Inc. which has piezoelectric properties (i.e. separates charges to each of two surfaces when mechanically stressed.) It is sandwiched between upper and lower flexible, electrically conductive metallic layers (1011, 1015) which collect and transmit the separated charges to positive and negative outputs (1021, 1022). Metallic layers (1011, 1015) may be formed by sputtering, for example with a NiCu amalgam or by silkscreening with a metal such as silver. For large scale production any known method of lightly coating a nonconductive material can be used, several of which are used in production of integrated circuits and metallized films such as MYLAR. An electrically nonconductive material (1017) is used to house the film (1013), metallic layers (1011, 1015), and outputs (1021, 1022). Additionally the housing has a central chamber (1019) which is filled with air, gas or other elastomeric component which is electrically nonconductive. Since pressure in the chamber (1019) is relatively constant, no pump is required. The lower metallic layer is protected by a neutral layer (1009), preferably of a material which can be disinfected, ie. by swabbing with alcohol. One such material is chromium (electrical resistivity=12.9 microhm-cm.).

The sensor rests on the surface (1007) of a flexible environment (1001) such as skin. Located in the environment (1001) is a tube (1003) such as an artery, which has flowing through it a fluid (gas or liquid) (1005) such as blood. As fluid (1005) pulses in the tube (1003) it exerts varying pressure on the film (1013) causing measurable differences in electrical potential (voltage) between the positive and negative outputs (1021, 1022).

Figure 2:
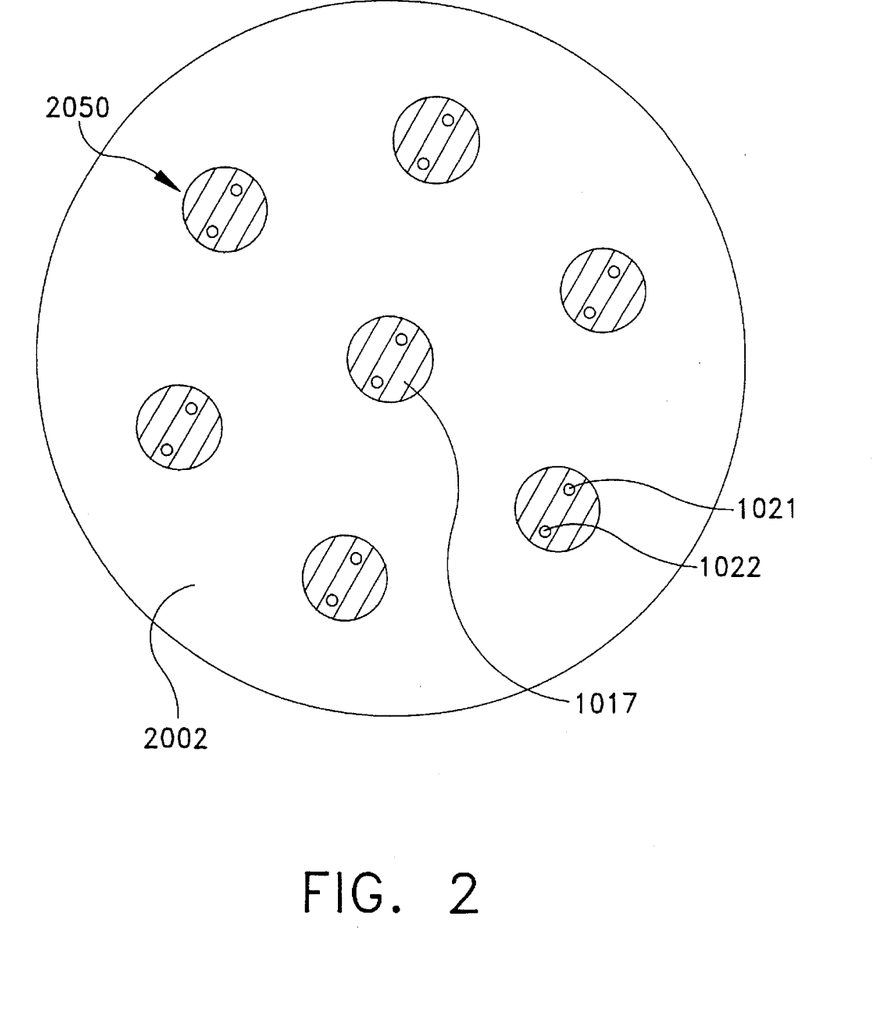
FIG. 2 is an overhead view of a sensor array for use in measuring blood pressure.

For measuring blood pressure, an array of sensors (seven in the example shown) is located in an electrically nonconductive casing (2002) as shown in FIG. 2. The casing is made of a supportive material which isolates reception of each sensor from other sensors. Outputs of the sensors are connected to inputs s1, s2, s3, s4, s5, s6 and s7 of the circuit as shown in FIGS. 3 and 4.

Figure 7:
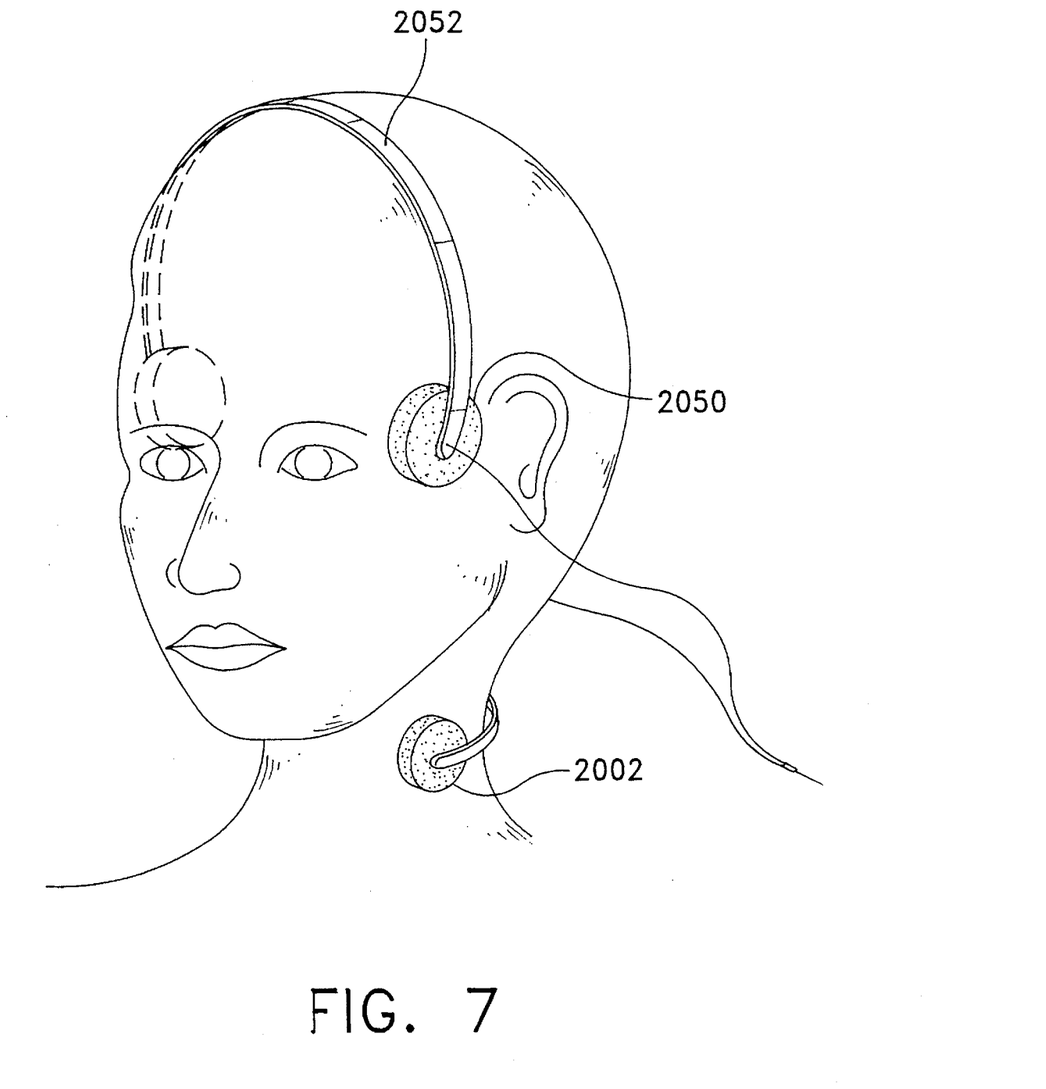
FIG. 7 shows a device measuring right and left temporal blood pressures.

Each casing can be held in a selected location on the subject by a variety of means, including taping, hook and loop closing wrap (using VELCRO brand fasteners), installation on an elastic or U-shaped band (2052), or hand held, for example without distorting the artery. FIG. 7 shows an arrangement which can be used easily for measuring left and right carotid or temporal blood pressure. Since both sides can be measured simultaneously, unbalance is readily detected.

Figure 3:
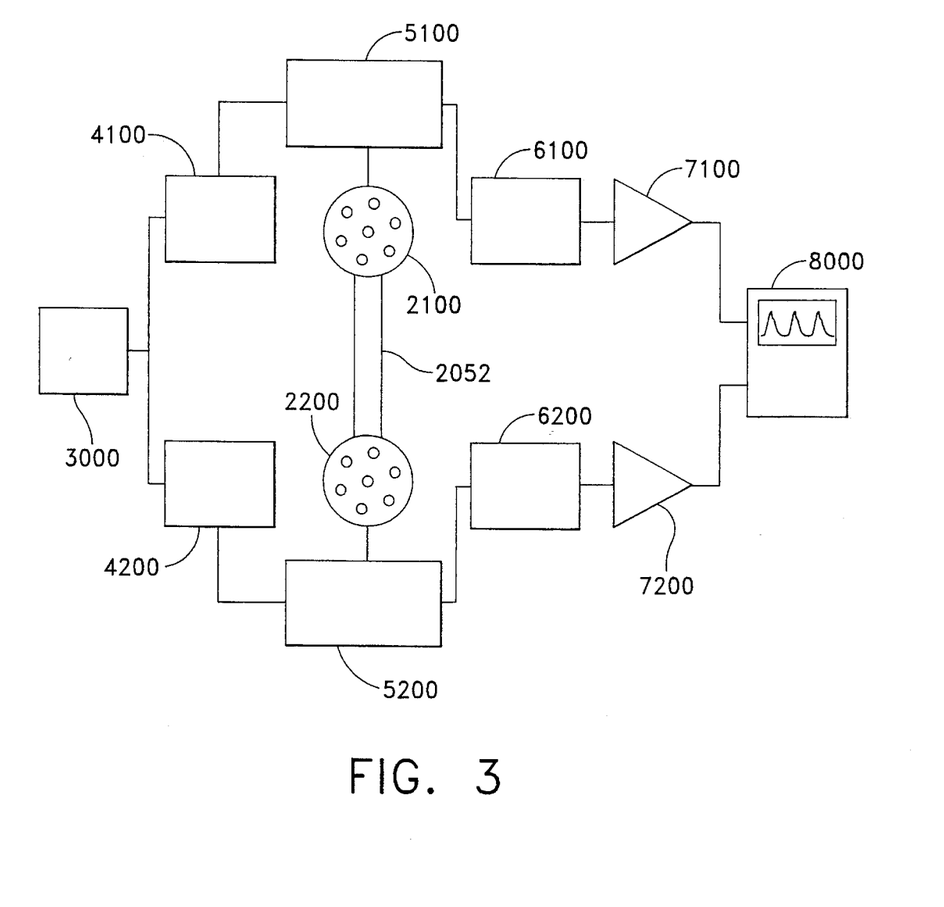
FIG. 3 is a block diagram of circuitry for use with the sensor array shown in FIG. 2.
Figure 4A:
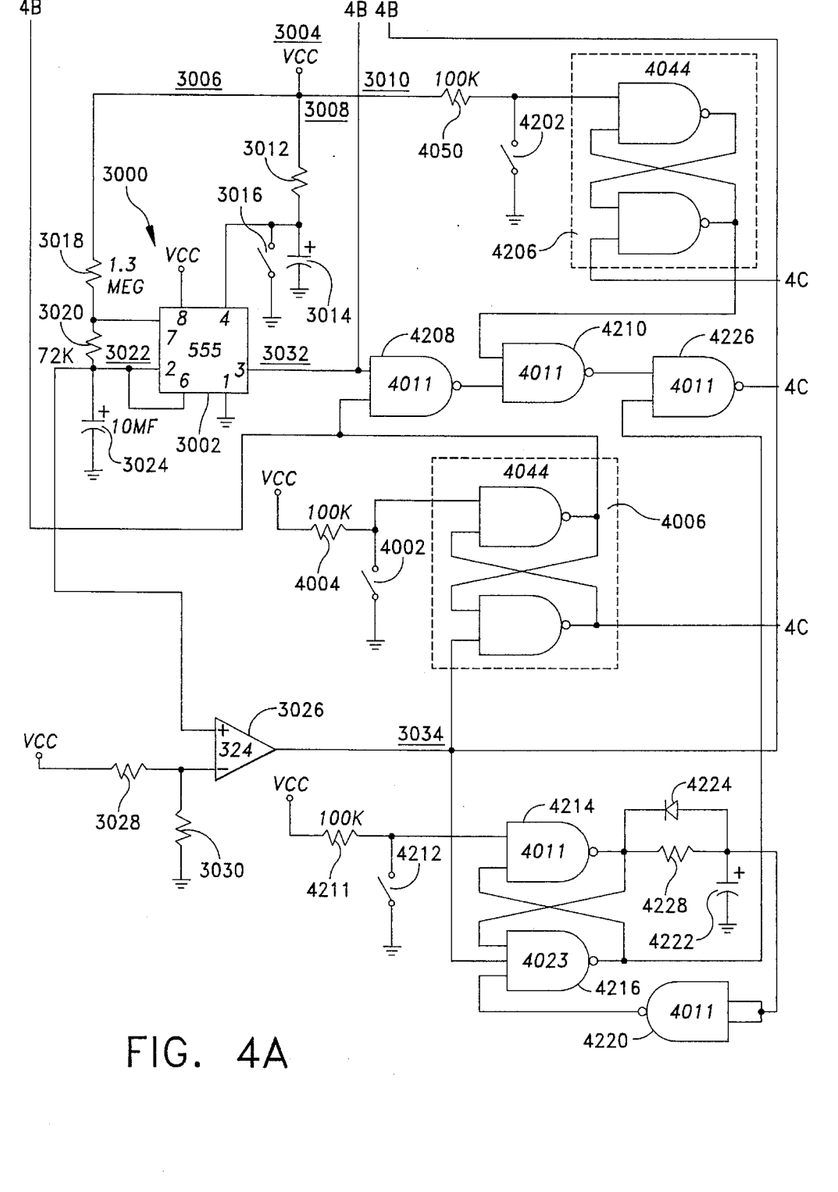
FIGS. 4A–4H detail the circuit of FIG. 3.
Figure 4B:
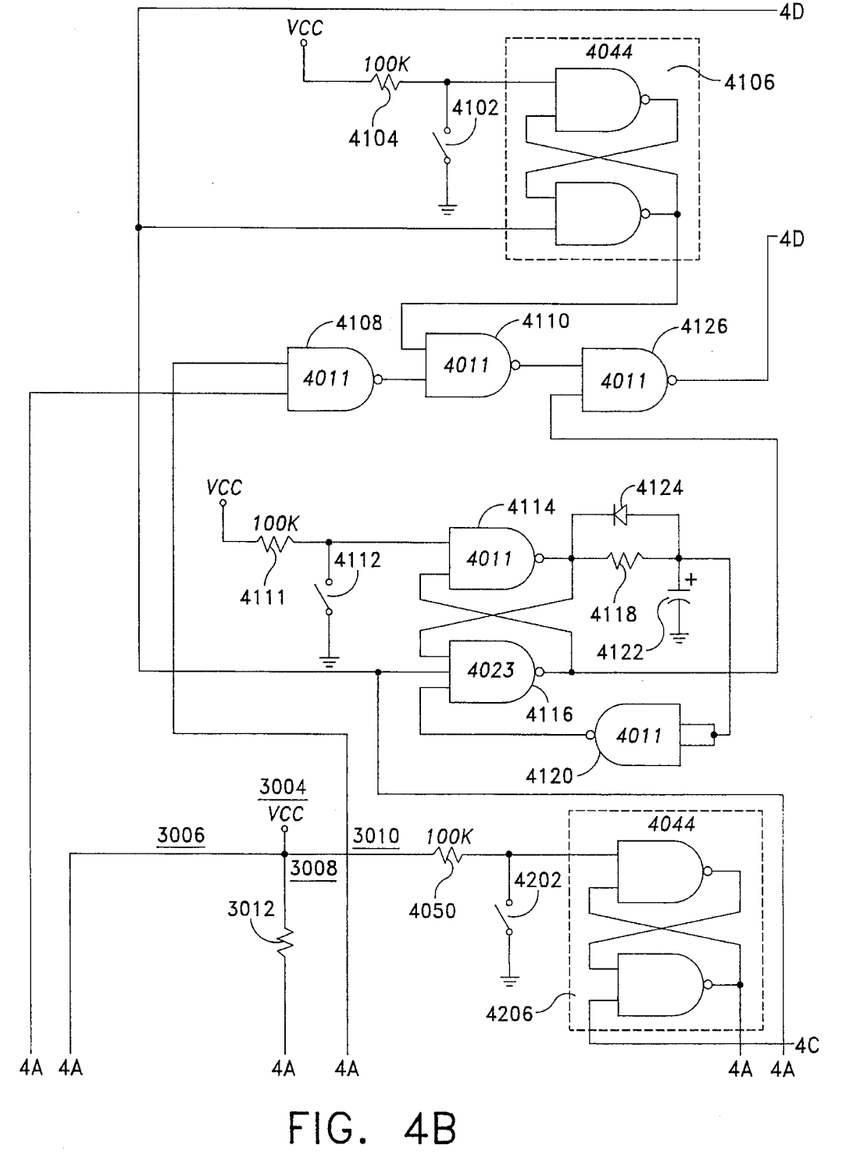
Figure 4C:
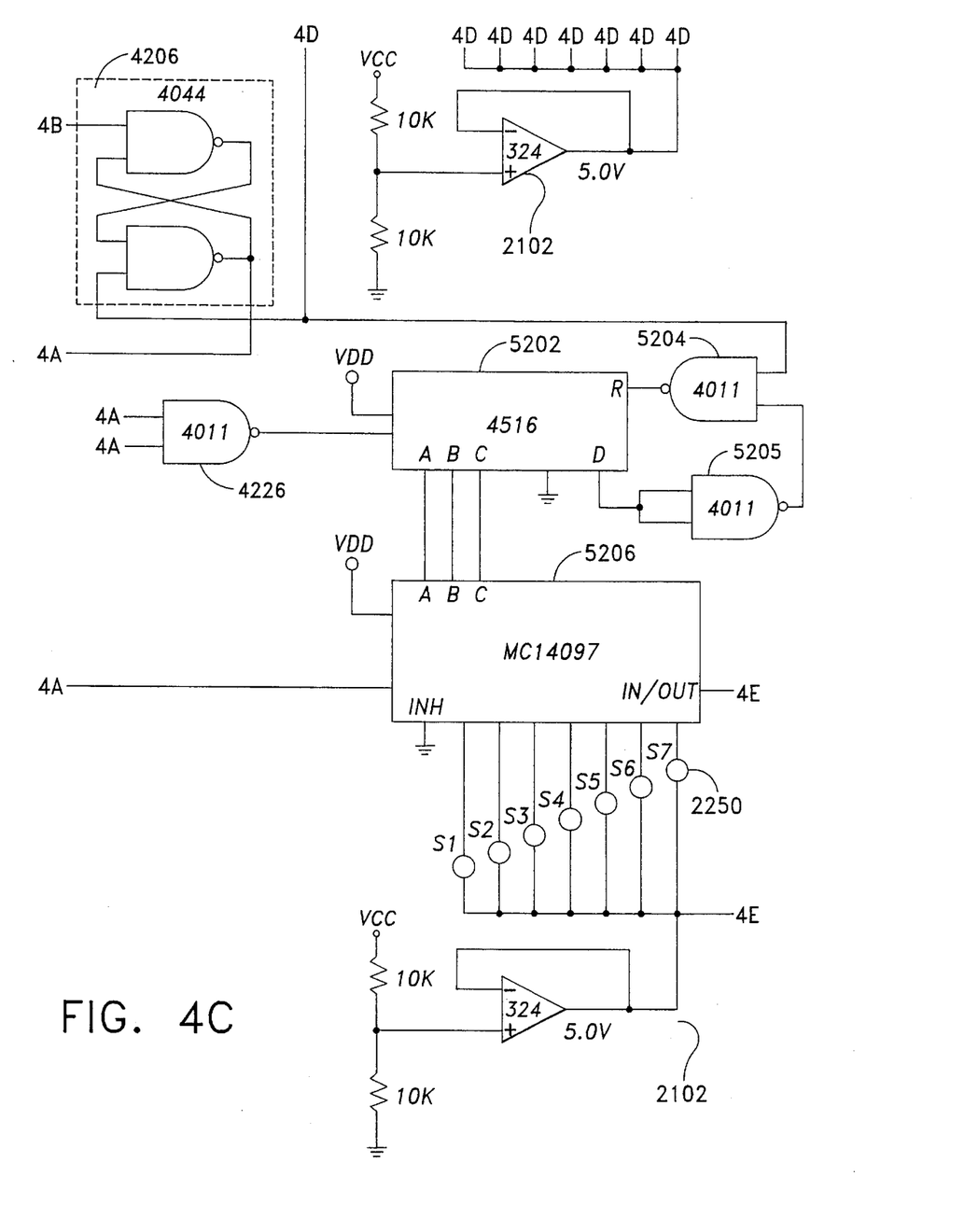
Figure 4D:
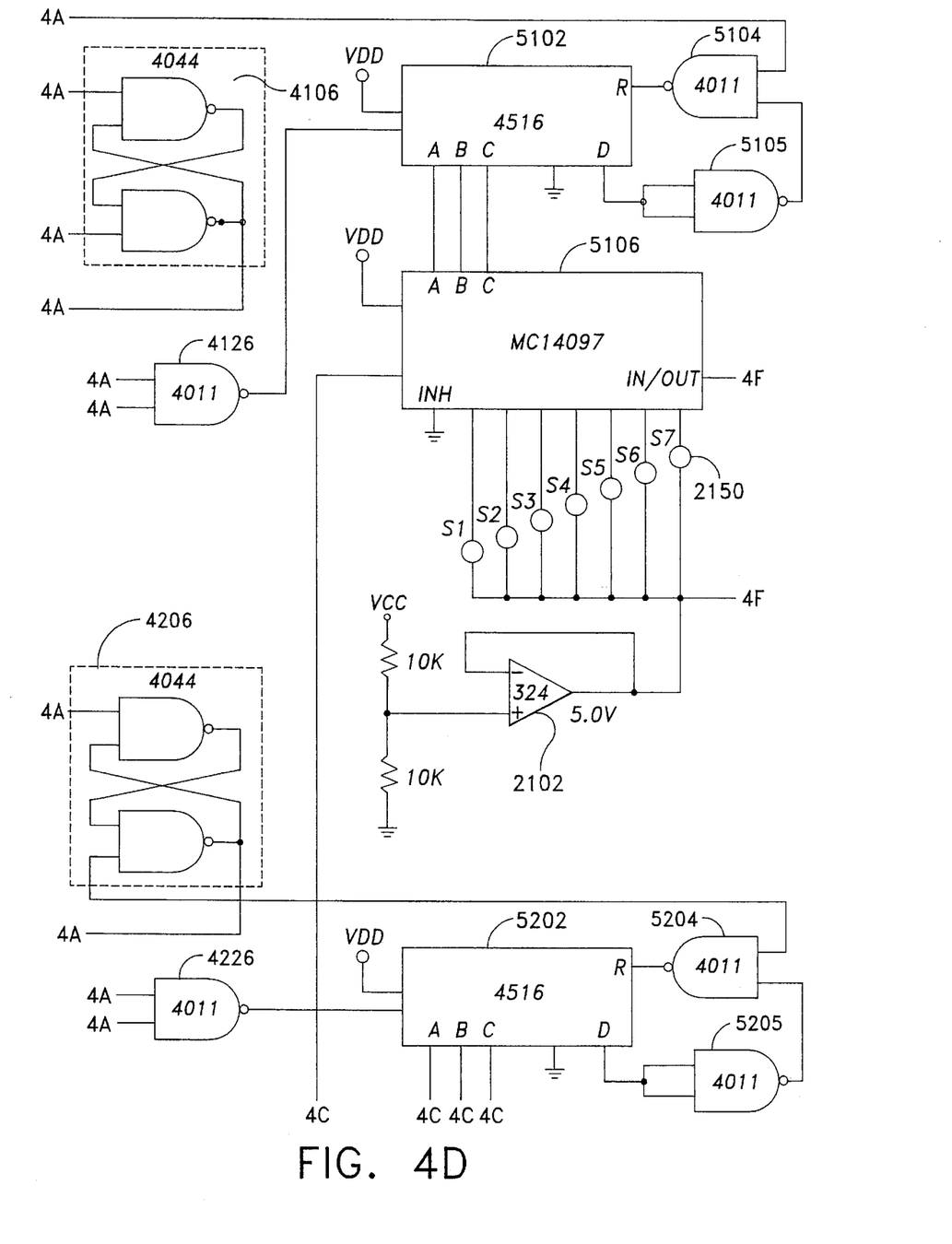
Figure 4E:
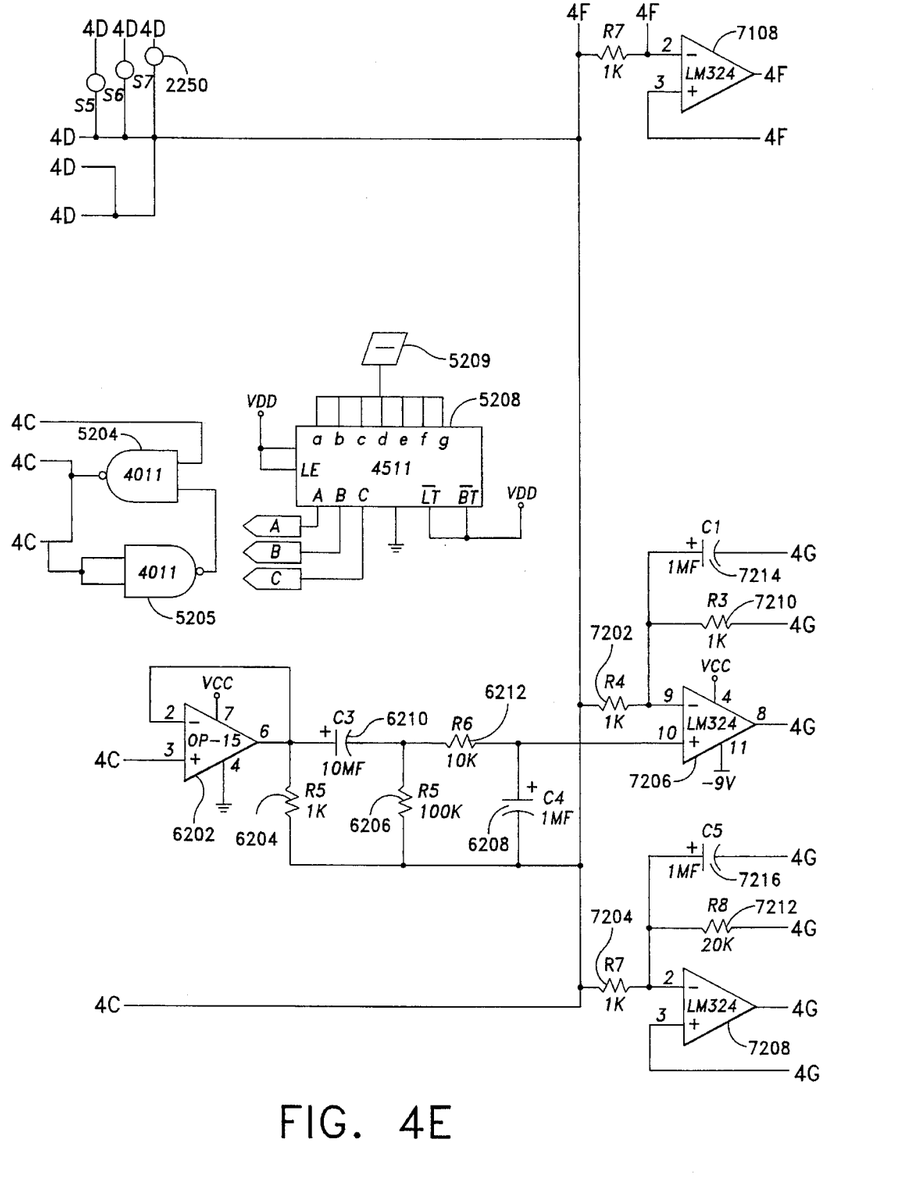
Figure 4F:
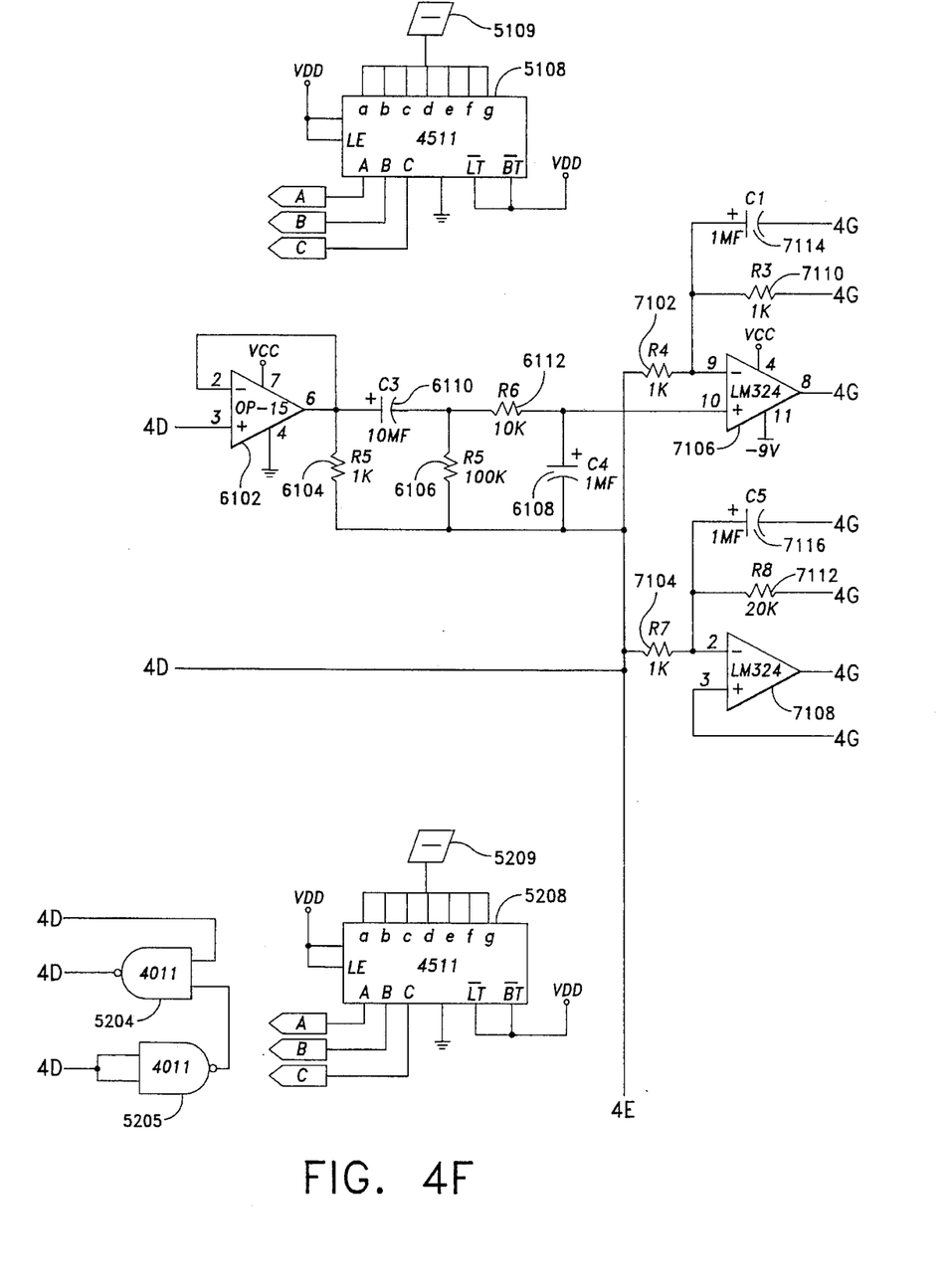
Figure 4G:
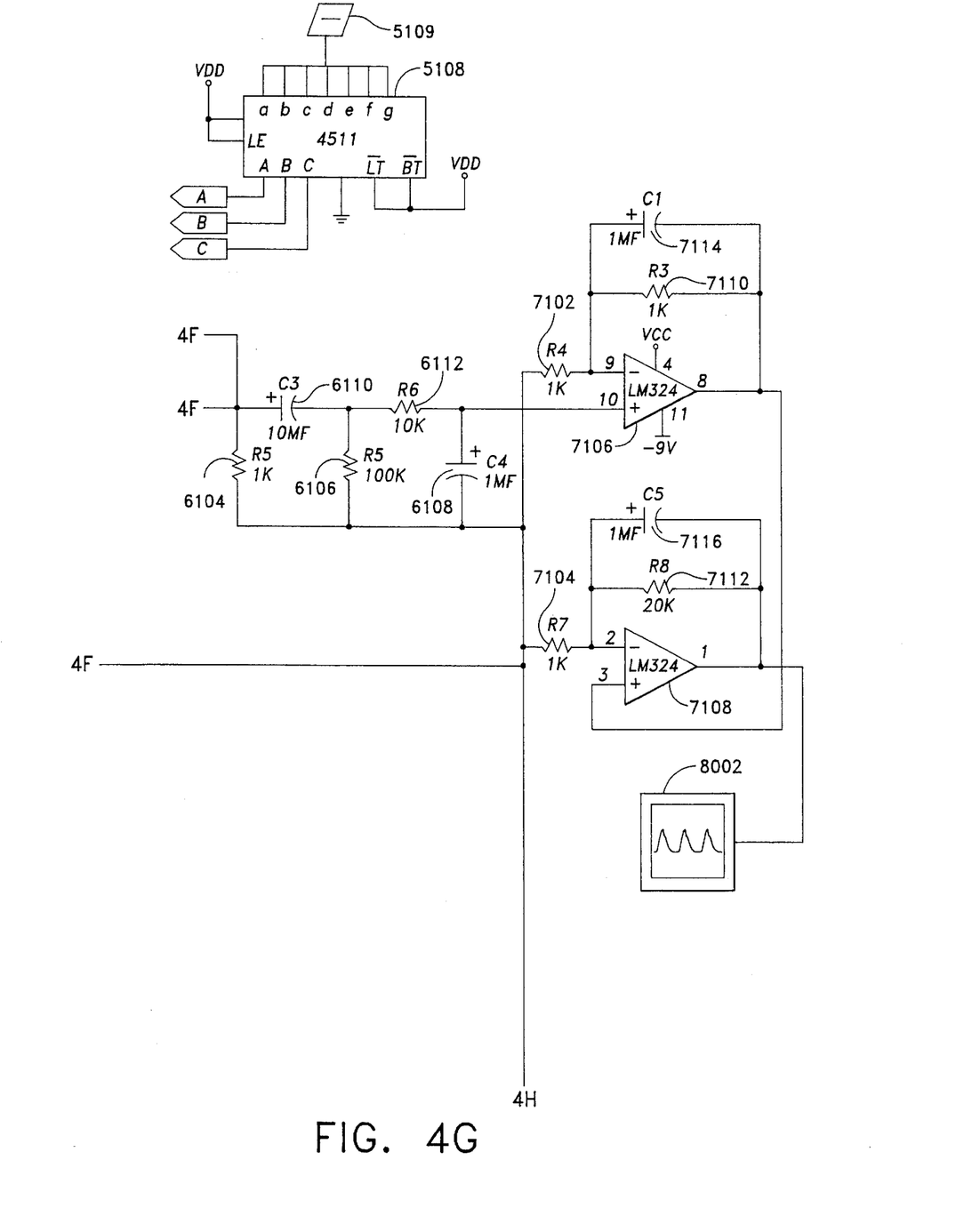
Figure 4H:
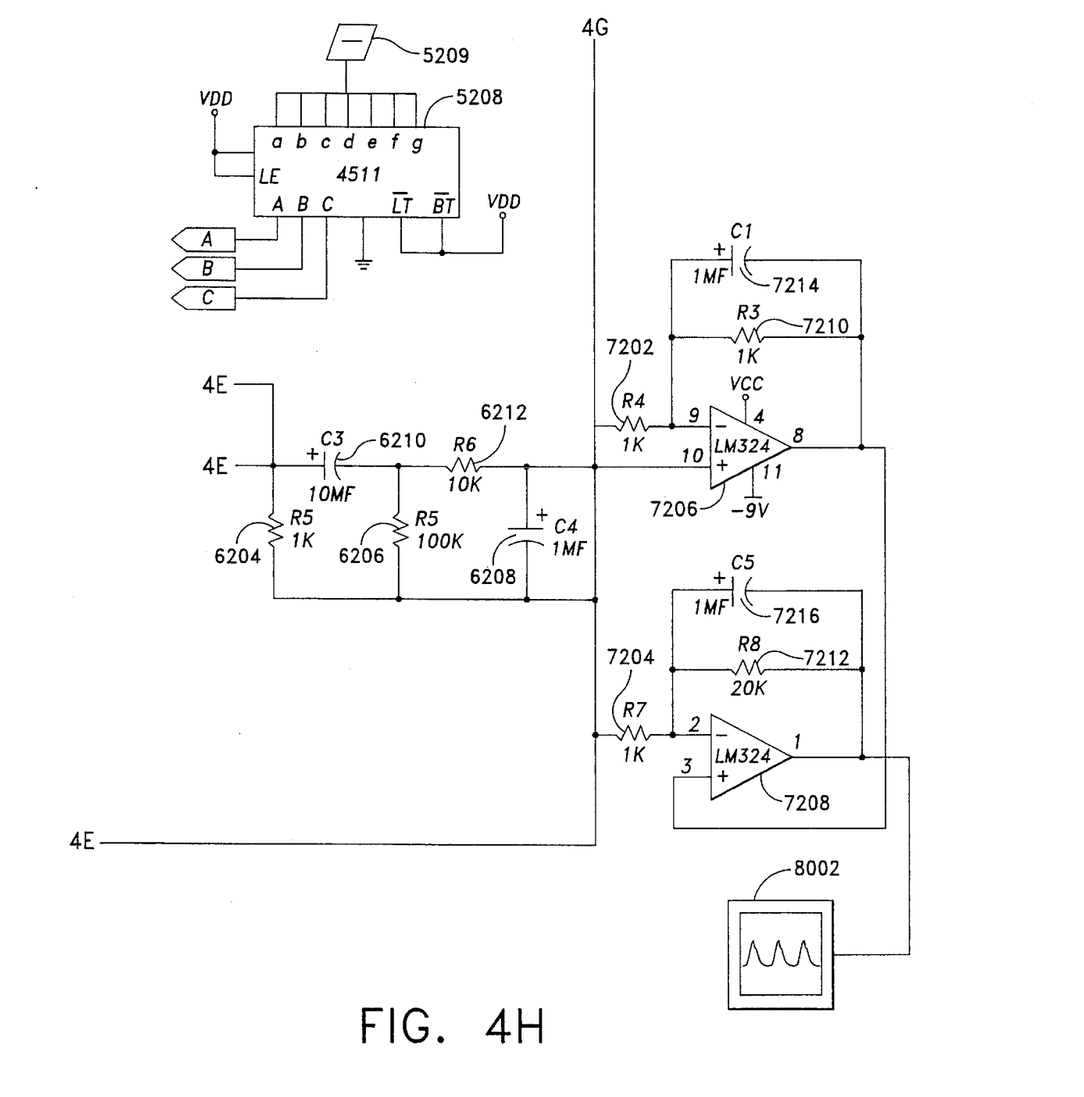

The circuit of FIG. 3 is suitable for use with a dual array such as pictured in FIG. 7. A master timing circuit (3000) has an output which is split into signals traveling to right and left logic gates (4100, 4200). Output from right and left sensor arrays (2100, 2200) and from logic gates (4100, 4200) is processed into a sequential output by right and left sequencers (5100, 5200). The sequential output passes through right and left filters (6100, 6200); amplifier-drivers (7100, 7200); and then to a display (8000).

The master timing circuit is controlled by a 555 timer (3002) grounded at pin 1, connected to a voltage source at pin 8, a master reset at pin 4, and has discharge, threshold, and trigger lines connected at pins 7, 6, and 2 respectively. The master reset has a system supply voltage (3004) which feeds three lines (3006, 3008, 3010) The central line (3008)

has a resistor (3012), grounded capacitor (3014) and switch (3016). Closing the switch (3016) activates the system. A 1.3 MEG resistor (3018) is located on a line (3006) connecting the system supply current (3004) and discharge pin 7, and a 72K resistor (3020) is located in a line (3022) connecting discharge pin 7 with triggering pin 2. Between the resistor (3020) and triggering pin 2 is a line connecting that line (3022) with threshold pin 6. That line (3022) is grounded through a 10 MF (3024) capacitor and branches to the anode of a 324 amplifier (3026). A resistor (3028) is located between a supply voltage and the cathode of the amplifier (3026) and the line is grounded through another resistor (3030).

The output of the master timing control leaves the 555 timer at pin 3 through a line (3032) which branches to the right and left logic gates (4100, 4200). The output of the amplifier (3026) flows to the logic gates (4100, 4200) and sequencing systems (5100, 5200) over a branched line (3034). This configuration allows the master timer (3000) to set the system to a predetermined starting value each time the system is turned on or in case of power interruption, and start an automatic sensor selection process.

Right and left circuits after the master timing system (3000) are essentially identical, and the system can easily be adapted to one or several sensor arrays. The right logic gate (4100) has a manual switch (4102) connected to the supply voltage through a 100K resistor (4104) for overriding the master system. Output from this manual switch (4102) and from the amplifier (3026) are inputs to a 4044 MOS SR (set-reset) flip flop (4106). Output from the 555 timer (3002) and from a line connecting the left flip flop (4206) are fed to a first 4011 NAND gate (4108) to choose either manual or automatic mode. Output from the first NAND gate (4108) and from the SR flip flop (4106) become inputs to a second 4011 NAND gate (4110). The logic gate (4100) also has a manual clock with a manual switch (4112) connected to the supply voltage through a 100K resistor (4111). A normally open master switch (4002) grounds input voltage which has passed through a 100K resistor (4004) when closed. This input enters a main 4044 SR flip flop (4006) along with input from branched line (3034). Output from the main flip flop (4006) feeds into the multiplexer-counter system (5100, 5200). When the right switch (4112) is closed, current flows to ground and the input into a first 4011 NAND (4114) gate of a modified flip flop drops to low; if it is open, the input is high. A 4023 3 input NAND gate (4116) has input from the amplifier (3026) which is alternating between high and low; input from the first NAND gate (4114) and input which is lower than direct output from the NAND gate (4114) under automatic clock conditions since it travels through a resistor (4118) and into a second 4011 NAND gate (4120) via a branched input. Since both inputs would then be low, output of the NAND gate (4120) is high. However, closing the manual clock switch 4112 causes a change in strength since a capacitor (4122) is already in a discharged state and is charged through a resistor (4118) causing an input on the 4023 gate (4116) to change to low. A diode (4124) in located in parallel with the resistor (4118) with the anode toward the capacitor (4122). By choosing a momentary switch for the manual switch (4112), a one shot effect is achieved, that is, each closure of the switch (4112) puts out only one pulse, enabling selection of sensors from an array to be done manually. Output from the 4023 NAND gate (4116) and second SR NAND gate (4110) become input for a final 4011 NAND gate (4126) output of which is either an alternating automatic signal or an alternating signal which is manually controlled. This output is fed into a 4516 BCD (binary coded decimal) counter (5102) in the sequencer (5000). Output from the master timer (3000) is fed into one port of a NAND gate (5104), output of which is connected to the reset pin of the counter (5102). The D output pin is connected by a branched connector to another NAND gate (5105), output of which is connected to the other port of the NAND gate (5104). The counter is set to count to 7 (sampling each sensor in the array) and start over. Output from the counter is fed to a MC14097 Multiplexer (5106) and 4511 BCD to a 7 segment decoder driver (5108), operating a 7 segment number display (5109), thus indicating the sensor being sampled at any given time. The multiplexer (5106) takes output from the counter (5102), samples output from corresponding sensors (s1, s2, s3, s4, s5, s6, or s7), and input from the left SR flip flop (4206) controlled by the left manual override (4202). Output from the multiplexer (5106) is fed into the system wave filter (6100). The first component of the filter is an OP-15 buffer amplifier (6102). The signal then passes through a bandpass filter which selects low frequencies (i.e. 1–100 cps). The filter has a 1K resistor (6104), a 100K resistor (6106), and a 1 MF (6108) capacitor arranged in parallel as shown in FIG. 4. Located between the resistors (6104, 6106) is a 10 MF capacitor (6110) and between the second resistor (6106) and the 1 MF (6108) capacitor is a 10K resistor (6112). The sensor system (2100)—consisting of sensors (2150) and a voltage reference (2102)—supplies the input to sensor (2050) and allows detection of system voltage fluctuations. The voltage reference (2102) is also connected to analog amplifiers (7100, 7200) after passing through two 1K resistors (7102, 7104). Output from the first resistor (7102) is fed through a branched line to the cathode of an LM324 operational amplifier (7106) and a circuit connected to the output of the amplifier (7106) by a 1K resistor (7110) and a 1 MF capacitor (7114) in parallel. Output from the upper line of the bandpass filter is input for the amplifier (7106) anode. Output from the second resistor (7104) is fed through a branched line to the cathode of an LM324 operational amplifier (7108) and a circuit connected to the output of the amplifier (7108) by a 20 K resistor (7112) and a 1 MF capacitor (7116) in parallel. Output from the first amplifier (7106) is input for the anode of the second amplifier (7108). Output from the second amplifier (7108) is fed to a computer (8002) for analysis by software and display and/or printing of a hard copy. The computer (8000) shows output of each sensor as it is automatically sampled. Using the manual clock switch (4112) allows the operator to focus on a single sensor or control the rate of selection.

The left logic gate (4200) has a manual switch (4102) connected to the system voltage through a 100K resistor (4050). Output from this manual switch (4102) and from the amplifier (3026) are inputs to a 4044 MOB SR (set-reset) flip flop (4206). Output from the 555 timer (3002) and from a line connecting the flip flop (4206) are fed to a 4011 NAND gate (4208). Output from the NAND gate (4208) and from the SR flip flop (4206) become inputs to a 4011 NAND gate (4210). The logic gate (4200) also has n manual clock with a manual switch (4212) connected to the supply voltage through a 100K resistor (4211). A 4023 3 input NAND gate (4216) has input from the amplifier (3026); input from the NAND gate (4214) and input which is lower than direct output from the NAND gate (4214) under automatic clock conditions since travels through a resistor (4228) and into a second 4011 NAND gate (4220) via a branched input. A diode (4224) in parallel with the resistor (4228) with the anode toward a capacitor (4222), which when charged through a resistor (4228) causes an input on the 4023 gate (4216) to change to low. Output from the 4023 NAND gate (4216) and second SR NAND gate (4210) become input for a final 4011 NAND gate (4226). This output is fed into a 4516 BCD (binary coded decimal) counter (5202) in the sequencer (5000). Output from the master timer (3000) is fed into one port of a NAND gate (5204) output of which is connected to the reset pin of the counter (5202). The D output pin is connected by a branched connector to another NAND gate (5205), output of which is connected to the other port of the NAND gate (5204). Output from the counter is fed to a MC14097 Multiplexer (5206) and 4511 BCD to a 7 segment decoder driver (5208), operating a 7 segment number display (5209), thus indicating the sensor being sampled at a given point. The multiplexer (5206) takes output from the counter (5102); samples output from corresponding sensors (s1, s2, s3, s4, s5, s6, or s7), and input from the right SR flip flop (4106) controlled by the left manual override (4102). Output from the multiplexer (5206) is fed into the system wave filter (6200). The first component of the filter is an OP-15 buffer amplifier (6202). The signal then passes through a bandpass filter which selects low frequencies (i.e. 1–100 cps). The filter has a 1K resistor (6204), a 100K resistor (6206), and a 1 MF (6208) capacitor arranged in parallel as shown in FIG. 4. Located between the resistors (6204, 6206) is a 10 MF capacitor (6210) and between the second resistor (6206) and the 1 MF (6208) capacitor is a 10K resistor (6212). The sensor system (2200)—consisting of sensors (2250) and a voltage reference (2202)—supplies the input to sensor (2050) and allows detection of system voltage fluctuations. The voltage reference (2202) is also connected to analog amplifiers (7100, 7200) after passing through two 1K resistors (7202, 7204). Output from the first resistor (7202) is fed through a branched line to the cathode of an LM324 operational amplifier (7206) and a circuit connected to the output of the amplifier (7206) by a 1K resistor (7210) and a 1 MF capacitor (7214) in parallel. Output from the upper line of the bandpass filter is input for the amplifier (7206) anode. Output from the second resistor (7204) is fed through a branched line to the cathode of an LM324 operational amplifier (7208) and a circuit connected to the output of the amplifier (7208) by a 20K resistor (7212) and a 1 MF capacitor (7216) in parallel. Output from the first amplifier (7206) is input for the anode of the second amplifier (7208). Output from the second amplifier (7208) is fed to a computer (8002) for analysis by software and display and/or printing of a hard copy.

The continuous output of data allows comparison of data produced simultaneously by multiple sensor arrays placed at selected locations on the subject.

Since comparison of curves is presently available through software, it is foreseen that an exemplar curve (or curves) could be stored and accessed, and the sensor within each array having the most desired similarity be selected automatically for display, enabling the operator to select sensors which are best positioned to achieve the operator's goals. Algorithms for curve fitting can be found in many books. Programs which are presently available which could be adapted for the curve comparison are sold under the names MATHCAD and TABLECURVE. TABLECURVE curve fitting software is a product of Jandel Scientific. To adapt the TABLECURVE software, a "normal" curve could be analyzed and placed into the selection of x,y curves, and then all new curves analyzed from this synthesized x,y curve.

Time intervals between repeated events, such as first pressure upon contraction of the heart muscle in each successive sequence can be measured to obtain a pulse rate, and also to demonstrate the pulse frequency between contractions and variations in the timing and intensity of each pulsation.

The device can be combined with other sensors, such as thermistors, to measure additional variables such as skin temperature at various locations and core temperatures both by correlation of skin-to-core temperatures and direct measurement of core temperatures on accessible target organs.

Figure 5A:
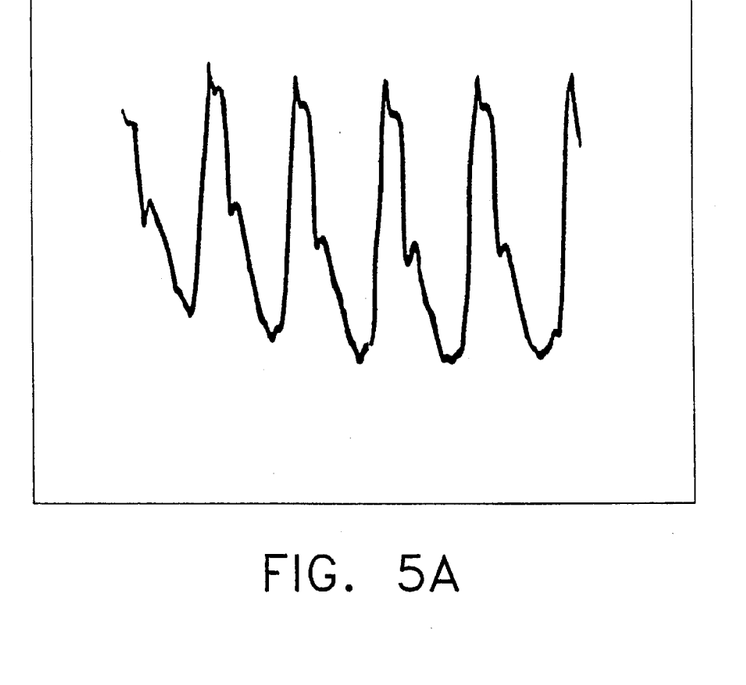
FIGS. 5A and 5B are outputs from a carotid artery.
Figure 5B:
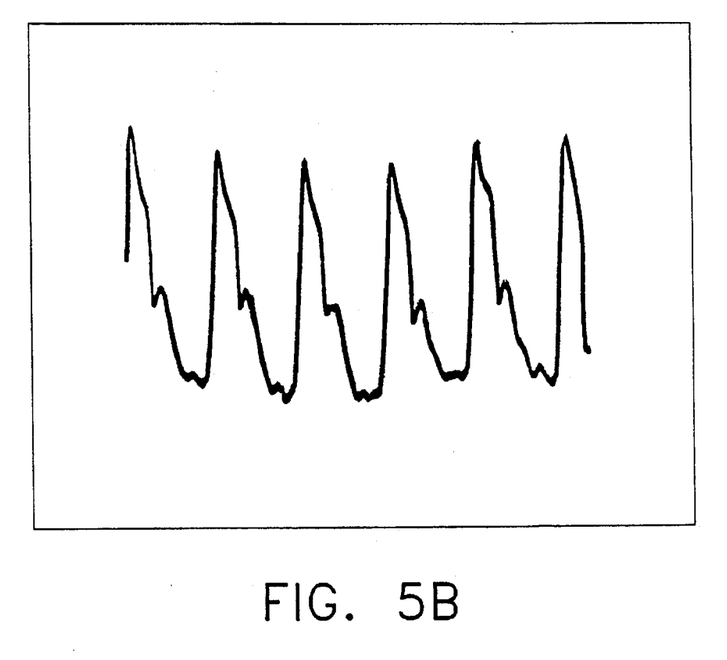

FIGS. 5A and 5B each displays actual outputs from a working prototype of the invention generated by placing the sensor element over a carotid artery in a human subject at different occasions.

Figure 6A:
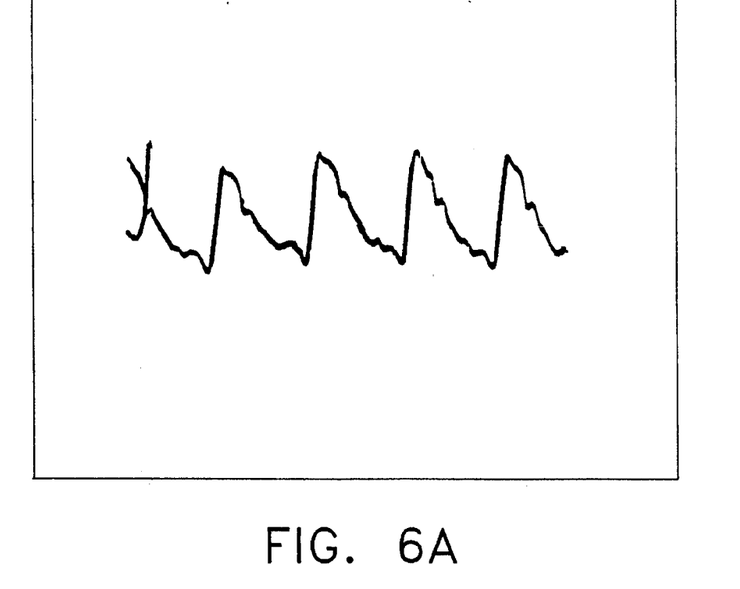
FIGS. 6A and 6B are outputs from temporal arteries.
Figure 6B:
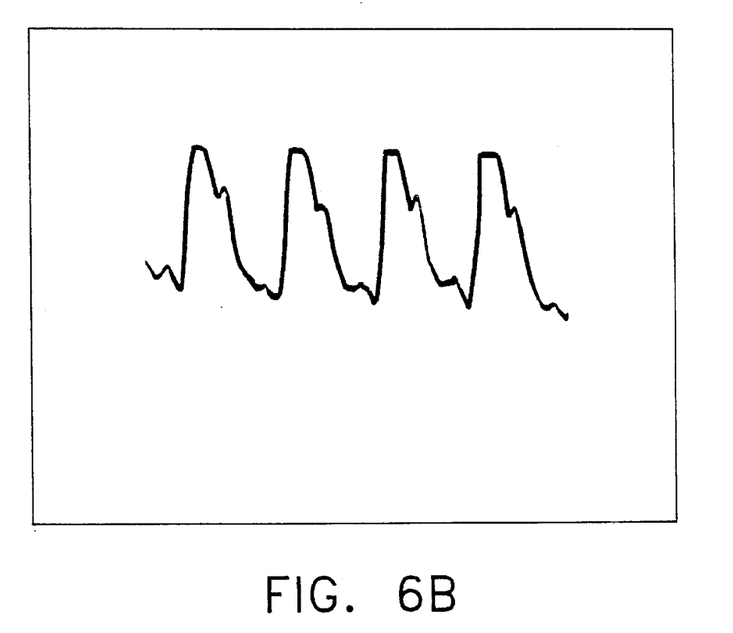

FIGS. 6A and 6B respectively display actual outputs from working prototypes of the invention generated by placing the sensor element over a left temporal and also, over a right temporal artery in a human subject at different occasions.

This invention provides a flexible system which can be used for a wide variety of applications and requires minimal skill to obtain a continuous measurement of blood pressure. The sensor is useful for a variety of applications involving differential pressure, including industrial flow through tubes to sense blockage, e.g. in Nuclear Energy facilities.

Another medical application is location of lumps such as tumors. For example, in manual breast examination, pressure is applied and resistance to the pressure is felt for variations. With this invention sensors could be arranged in a cup, pressure applied to fill the cup and make contact with the sensors, and variations in resistance mapped for analysis. Other arrays could be used for detection of such problems as potential and developing hernias and aneurysms.

Other arrays can be used to detect potential and existing ruptures in hoses.

This invention can measure pressure aspects of liquids and gases pumped from one source to another, as in transport of liquids and gases through pipelines, including the small conduit pipes bringing fuel oil from tank to precombustion chambers in diesel engines.

This invention permits the creation of selective data reporting and display such as diastolic, systolic, and mean blood pressure; and specific Korotkoff positions such as Korotkoff V for neonates.

What is claimed is:

1. A piezoelectric sensor comprising:

a housing having a chamber, said chamber having only one opening;

a flexible piezoelectric material having first and second sides covering said opening;

a compressible fluid within said chamber; and means for measuring electrical charges on said first side.

2. The sensor of claim 1 further comprising:

means for measuring electrical charges on said second side.

3. The sensor of claim 2 further comprising:

an electrically neutral, flexible protective covering located over said flexible piezoelectric material.

4. The sensor of claim 2 wherein said material further comprises:

a flexible nonconductive film having a conductive layer.

5. The sensor of claim 4 wherein said conductive layer is metallic.

6. The sensor of claim 4 wherein said material further comprises:

a second conductive layer.

7. An apparatus for surface measurement of pressure change within a flexible environment comprising:

at least one piezoelectric sensor comprising:
  a chamber having a single opening located in a housing; and a
  flexible piezoelectric material having a first side and a second side covering said opening;
  compressible fluid within said chamber;
  means for measuring electrical charge on said first and second sides; and
  means for reporting output from said first and second measuring means.

8. The apparatus of claim 7 further comprising:
a first array of piezoelectric sensors.

9. The apparatus of claim 8 wherein said reporting means further comprises:
  display means chosen from the group consisting of video screens and printers.

10. The apparatus of claim 9 further comprising:
  means for reporting said output as a function of time.

11. An apparatus for surface measurement of pressure change within a flexible environment comprising:
  a first array of piezoelectric sensors, said sensors comprising:
    a chamber having a single opening located in a housing; and
    a flexible piezoelectric material having a first side and a second side covering said opening;
  compressible fluid within said chamber; and
    means for measuring electrical charge on said first and second sides;
  means for reporting output from said means for measuring, said means for reporting output further comprising:
    a display means chosen from the group consisting of video screens and printers;
    means for reporting said output as a function of time; and
  means for measuring and reporting surface temperature of said environment.

12. The apparatus of claim 9 wherein said reporting means further comprises:
  a signal processor.

13. The apparatus of claim 12 wherein said signal processor further comprises:
  signal identification means;
  signal amplification means; and
  signal selection means.

14. The apparatus of claim 9 wherein said signal processor further comprises:
  means for determining and reporting time intervals between repeated events.

15. The apparatus of claim 8 further comprising a second array of sensors.

16. The apparatus of claim 15 wherein said first and second array of sensors are located at the terminals of a U shaped band.

17. A method for surface measurement of pressure change within a flexible environment comprising:
  placing a sensor having flexible piezoelectric material over a sole opening of a chamber containing a compressible fluid onto the surface of said flexible environment;
  measuring electrical charge on said material; and reporting output of said electrical change.

18. The method of claim 17 further comprising the step of:
  measuring time and said reporting step further comprises reporting said charge change as a function of time.

19. A method for surface measurement of pressure change within a flexible environment comprising:
  placing a sensor having flexible piezoelectric material over a sole opening of a chamber containing a compressible fluid onto the surface of said flexible environment;
  measuring electrical charge on said material;
  reporting output of said electrical change;
  measuring the temperature of said surface; and
  reporting said temperature measurement.

20. The method of claim 18 wherein said reporting step further comprises:
  identifying electrical signals;
  amplifying said signals; and
  selecting signals for reporting.

21. The method of claim 20 further comprising:
  comparison of said selected signals to an exemplar signal.

* * * * *